US012788513B2

(12) United States Patent
Azizian et al.

(10) Patent No.: US 12,788,513 B2
(45) **Date of Patent: *Nov. 10, 2026**

(54) METHODS AND DEVICES FOR TELE-SURGICAL TABLE REGISTRATION

(71) Applicant: INTUITIVE SURGICAL OPERATIONS, INC., Sunnyvale, CA (US)

(72) Inventors: Mahdi Azizian, San Jose, CA (US); Jonathan M. Sorger, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,384

(22) Filed: May 19, 2025

(65) Prior Publication Data

US 2025/0275821 A1 Sep. 4, 2025

Related U.S. Application Data

(60) Division of application No. 17/410,725, filed on Aug. 24, 2021, now Pat. No. 12,329,480, which is a (Continued)

(51) Int. Cl.

*A61B 34/35* (2016.01)
*A61B 34/20* (2016.01)

(Continued)

(52) U.S. Cl.

CPC .............. *A61B 34/35* (2016.02); *A61B 34/30* (2016.02); *A61B 34/37* (2016.02); *A61B 90/98* (2016.02);

(Continued)

(58) Field of Classification Search

CPC ......... A61B 34/30; A61B 34/32; A61B 34/35; A61B 34/70; A61G 13/02; B25J 9/1692

See application file for complete search history.

(56) References Cited

U.S. PATENT DOCUMENTS 4,831,547 A 5/1989 Ishiguro et al.
5,177,563 A 1/1993 Everett et al.

(Continued)

FOREIGN PATENT DOCUMENTS

CN 113331948 A 9/2021
JP S63169278 A 7/1988

(Continued)

OTHER PUBLICATIONS

English language translation of Office Action mailed Jan. 22, 2019 for Japanese Application No. JP20160557631 filed Mar. 17, 2015, 23 pages (ISRG05550/JP).

(Continued)

*Primary Examiner* — Anhtuan T Nguyen
*Assistant Examiner* — Younhee Choi
(74) *Attorney, Agent, or Firm* — Haynes & Boone, LLP.

(57) ABSTRACT

A method comprises receiving at least one sensor reading that indicates a position or an orientation of a manipulator arm of a manipulator assembly when a keying feature of a distal portion of the manipulator arm is in contact with and received by a key receiving feature of a registration element of a table mounted registration device mounted to a side of a surgical table between a top surface and a bottom surface of the surgical table. The distal portion of the manipulator arm is movable in a plurality of degrees of freedom. The method further comprises determining, based on the received sensor reading, a spatial relationship between the manipulator assembly and the table mounted registration device; and reducing, by the table mounted registration (Continued)

device, the plurality of degrees of freedom when the table mounted registration device is in contact with and receives the distal portion of the manipulator arm.

19 Claims, 19 Drawing Sheets

Related U.S. Application Data continuation of application No. 15/126,480, filed as application No. PCT/US2015/020891 on Mar. 17, 2015, now Pat. No. 11,173,005.

(60) Provisional application No. 61/954,538, filed on Mar. 17, 2014.

(51) Int. Cl.

| | |
|---|---|
| ***A61B 34/30*** | (2016.01) |
| ***A61B 34/37*** | (2016.01) |
| ***A61B 90/98*** | (2016.01) |
| ***A61G 13/02*** | (2006.01) |
| ***G16H 40/63*** | (2018.01) |

(52) U.S. Cl.

CPC ............. *A61G 13/02* (2013.01); *G16H 40/63* (2018.01); *A61B 2034/2051* (2016.02); *A61B 2034/2055* (2016.02); *A61B 2034/2059* (2016.02); *A61B 2034/2061* (2016.02); *A61G 2203/30* (2013.01); *A61G 2205/60* (2013.01); *G05B 2219/40415* (2013.01); *G05B 2219/45119* (2013.01)

(56) References Cited

U.S. PATENT DOCUMENTS

| | | | |
|---|---|---|---|
| 5,224,680 | A | 7/1993 | Greenstein et al. |
| 5,400,638 | A | 3/1995 | Kim |
| 5,904,691 | A | 5/1999 | Barnett et al. |
| 6,070,109 | A | 5/2000 | McGee et al. |
| 6,615,112 | B1 | 9/2003 | Roos |
| 7,155,316 | B2 | 12/2006 | Sutherland et al. |
| 7,166,114 | B2 | 1/2007 | Moctezuma et al. |
| 7,166,144 | B2 | 1/2007 | Hein et al. |
| 7,979,159 | B2 | 7/2011 | Fixell |
| 8,369,983 | B2 | 2/2013 | Sato et al. |
| 8,400,094 | B2 | 3/2013 | Schena |
| 8,424,182 | B2 | 4/2013 | Sato et al. |
| 8,483,800 | B2 | 7/2013 | Jensen et al. |
| 9,289,181 | B2 | 3/2016 | Eder et al. |
| 9,358,682 | B2 | 6/2016 | Ruiz Morales |
| 9,381,641 | B2 | 7/2016 | Takahashi |
| 10,314,661 | B2 | 6/2019 | Bowling et al. |
| 10,874,467 | B2 | 12/2020 | Azizian et al. |
| 11,173,005 | B2 | 11/2021 | Azizian et al. |
| 12,329,480 | B2 | 6/2025 | Azizian et al. |
| 2002/0196906 | A1 | 12/2002 | Mun et al. |
| 2004/0054489 | A1 * | 3/2004 | Moctezuma De La Barrera ........ G16Z 99/00 702/105 |
| 2006/0025668 | A1 | 2/2006 | Peterson et al. |
| 2006/0161136 | A1 | 7/2006 | Anderson et al. |
| 2011/0098553 | A1 | 4/2011 | Robbins et al. |
| 2011/0166450 | A1 | 7/2011 | Peyrard et al. |
| 2012/0330154 | A1 | 12/2012 | Beasley et al. |
| 2013/0085510 | A1 | 4/2013 | Stefanchik et al. |
| 2013/0178870 | A1 | 7/2013 | Schena |
| 2013/0218137 | A1 | 8/2013 | Abovitz et al. |
| 2014/0024927 | A1 | 1/2014 | Piferi |
| 2014/0277722 | A1 | 9/2014 | Nagai et al. |
| 2015/0157416 | A1 | 6/2015 | Andersson et al. |
| 2016/0157887 | A1 | 6/2016 | Kim et al. |
| 2018/0289431 | A1 | 10/2018 | Draper et al. |
| 2021/0378770 | A1 | 12/2021 | Azizian et al. |

FOREIGN PATENT DOCUMENTS

| | | | |
|---|---|---|---|
| JP | H08137528 | A | 5/1996 |
| JP | 2012076188 | A | 4/2012 |
| WO | WO-2011060139 | A2 | 5/2011 |
| WO | WO-2013048957 | A1 | 4/2013 |

OTHER PUBLICATIONS

Extended European Search Report for Application No. EP15765677.8, mailed on Nov. 8, 2017, 10 pages (ISRG05550/EP).

International Search Report and Written Opinion for Application No. PCT/US15/20891, mailed on Jul. 1, 2015, 16 pages (ISRG05550/PCT).

Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

METHODS AND DEVICES FOR TELE-SURGICAL TABLE REGISTRATION

RELATED APPLICATIONS

The present application is a divisional of U.S. patent application Ser. No. 17/410,725, filed Aug. 24, 2021, which is a continuation of U.S. patent application Ser. No. 15/126,480, filed Sep. 15, 2016, now U.S. Pat. No. 11,173,005, which is the U.S. national phase of International Application No. PCT/US2015/020891, filed Mar. 17, 2015, which designated the U.S. and claims priority to and the benefit of U.S. Provisional Application No. 61/954,538, filed Mar. 17, 2014, the entire contents of each of which are incorporated herein by reference in their entirety.

U.S. patent application Ser. No. 15/126,480 is related to U.S. Provisional Application No. 61/954,559, entitled "Systems and Methods for Surgical Table Pose Tracking," filed Mar. 17, 2014, which is incorporated herein by reference in its entirety for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive tele-surgical systems have been developed to increase a surgeon's dexterity and avoid some of the limitations of traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more tele-surgical arms on each of which a surgical instrument is mounted. Operative communication between master controllers and associated manipulator arm and instrument assemblies is typically achieved through a control system. The control system typically includes at least one processor that relays input commands from the master controllers to the associated manipulator arm and instrument assemblies and back from the instrument and arm assemblies to the associated master controllers in the case of, for example, force feedback or the like. One example of a tele-surgical system is the DA VINCI® system available from Intuitive Surgical, Inc. of Sunnyvale, Calif.

A variety of structural arrangements can be used to support the surgical instrument at the surgical site during tele-surgery. The driven linkage or "slave" is often called a tele-surgical manipulator, and exemplary linkage arrangements for use as a tele-surgical manipulator during minimally invasive tele-surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the tele-surgical manipulator and the surgical instrument at the surgical site during tele-surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While such new telesurgical systems and devices have proven highly effective and advantageous, providing a wide range of configurations and coordinated movement between highly maneuverable manipulators, it can prove challenging to localize such movement in a surgical environment. Therefore, further improvements are desirable. It would be particularly beneficial if these improved technologies enhanced the efficiency and ease of use of tele-surgical systems. For example, it would be particularly beneficial to increase maneuverability, improve space utilization in an operating room, provide a faster and easier set-up, inhibit manipulator collision during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved tele-surgical devices, systems, and methods. Kinematic linkage structures and associated control systems described herein are particularly beneficial in performing minimally invasive surgical procedures on a patient. Such procedures often utilize interrelated and coordinated movement between multiple manipulators, each of which is highly configurable, having a range of alternative configuration for a given end effector position within the surgical environment. For various reasons, it may be desirable to position the patient in a particular position and/or orientation for a particular procedure. In addition, in some procedures, it may be further desirable to alter the position and/or orientation of the patient during a procedure. For example, certain patient positions and/or orientations may be particularly useful in accessing certain areas within the surgical workspace or it may be desirable for a patient to be disposed in particular alignments (e.g. inclined along one or more axes) during a procedure for various physiological reasons. Since many tele-surgical systems utilize a surgical table that is separate from the manipulator system and is often independently positionable along multiple degrees of freedom, various positions of the surgical table can present certain challenges during operation of tele-surgical manipulators, particularly in systems having multiple manipulators. Therefore, it would be desirable for such manipulator systems to have a means by which the surgical table can be "registered" with the manipulator assembly such that a spacial relationship between the surgical table and the manipulator assembly can be determined and utilized in calculating movement of the surgical manipulators. In one aspect, it would be desirable if such registration could be achieved through the use of existing features of the manipulator assembly. In another aspect, it would be useful if such registration could be performed dynamically such that the surgical table could be moved during a procedure without losing registration between the manipulator assembly and the table. In one aspect, the registration devices and methods described herein may be applied to various applications, including non-surgical applications, such as may be used in testing, simulations, and/or setup or in various industrial applications to register a supporting substrate with an adjacent manipulator or robotic assembly.

Methods of registration include determining a position and/or orientation of the surgical table relative the manipulator assembly based on a sense of a registration feature of the surgical table. The registration features may include various contact or non-contact means to determine a position and/or orientation of the surgical table relative to the manipulator assembly or relative to a common frame of reference. In one approach, the registration feature comprises a registration device mounted to the table at a particular location through which a manipulator of the assembly attaches to the table. The registration device is configured to constrain movement of the manipulator arm along one or more degrees of freedom that correspond to one or more degrees of freedom of the surgical table such that sensed joint states of the manipulator attached to the table through the device can be used to determine a position and/or orientation of the device. In another approach, the registration feature may include one or more markers which can be sensed by a sensor external to the surgical table, linear encoders attached to the table, shape sensors, or various other features suitable for determining a spatial relationship between the surgical table and the manipulator assembly or external frame of reference.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the tele-surgical manipulator structure on a particular patient. Along with actively driven manipulators used to interact with tissues and the like during treatment, tele-surgical systems may have one or more kinematic linkage systems that are configured to support and help align the manipulator structure with the surgical work site. While the high degree of configurability of these kinematic systems offer many advantages and advanced features, it can be difficult to locate a location of a manipulator feature of the manipulator assembly with respect to a separate component, such as a surgical table, particularly when the surgical table is separately positionable from the manipulator assembly. Since it is often useful to position a patient in various orientations or alignments in preparation for or during a procedure, it is desirable if the manipulator assembly can be registered with the surgical table either during initial set-up, or during a procedure, so that a position and/or orientation of the surgical table relative to the manipulator assembly can be determined and potentially utilized in calculated manipulator movements or surgical table movements (either automatic or user driven). Such registration methods allow further utilization of various calculated movement of the manipulators described in related applications, including but not limited to various null-space movement and collision avoidance movements, and may further be used to determine a position and/or orientation of the surgical table to any manipulator or associated component of the manipulator assembly. In addition, the registration methods described herein may be used in conjunction with various other aspects and registration features, such as any of those described in U.S. application Ser. No. 14/101,769 filed on Dec. 10, 2013, entitled, “Collision Avoidance During Controlled Movement of Image Capturing Device and Manipulatable Device Movable Arms,” which is incorporated herein by reference in its entirety for all purposes. The systems, devices and methods described herein, while applied to these particular surgical systems, may be used with various different types of manipulator systems, in accordance with the aspects of the invention described herein.

Minimally Invasive Tele-Surgery

Figure 1:
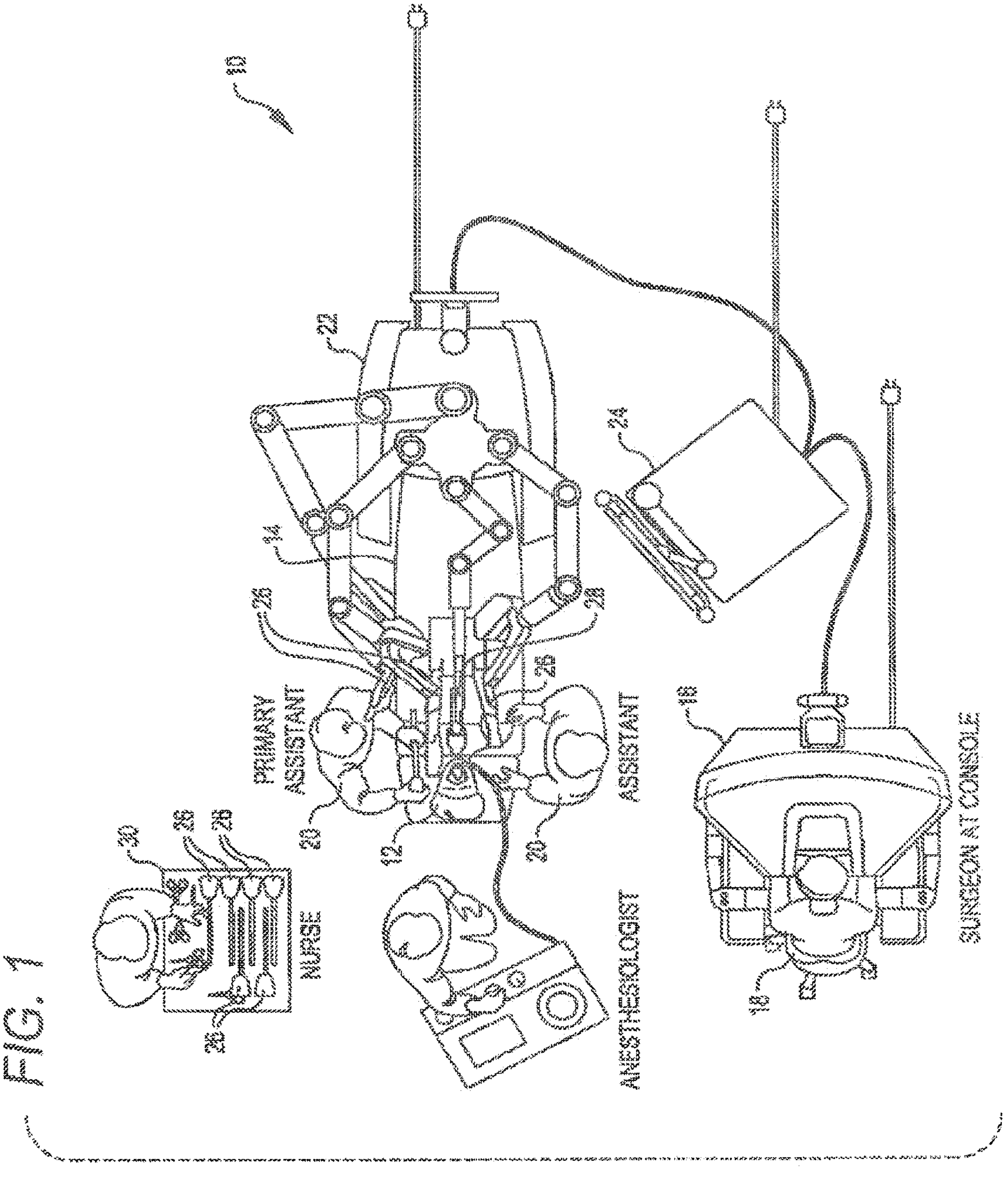
FIG. 1 is a plan view of a minimally invasive tele-surgical system being used to perform a surgery, in accordance with many embodiments.

Referring now to the drawings, in which like reference numerals represent like parts throughout the several views, FIG. 1 is a plan view illustration of a Minimally Invasive Tele-surgical (MIRS) system 10, typically used for performing a minimally invasive diagnostic or surgical procedure on a Patient 12 who is lying down on an Operating Table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a “tool”) through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
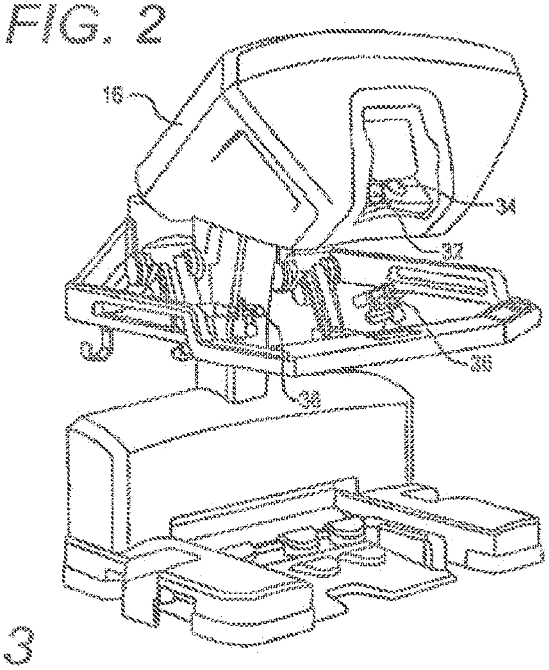
FIG. 2 is a perspective view of a surgeon's control console for a tele-surgical system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
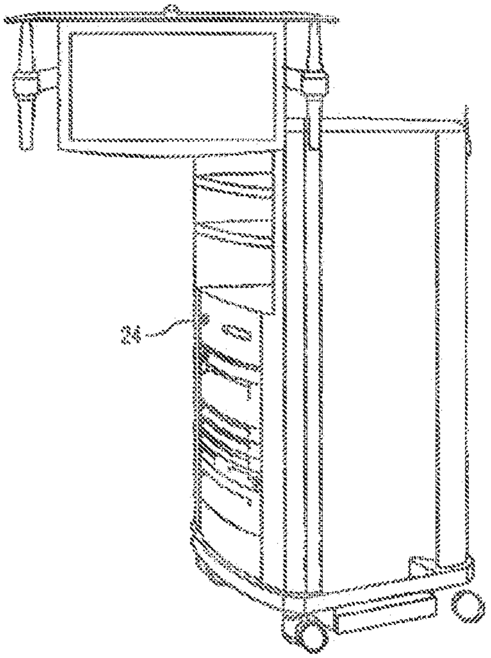
FIG. 3 is a perspective view of a tele-surgical system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
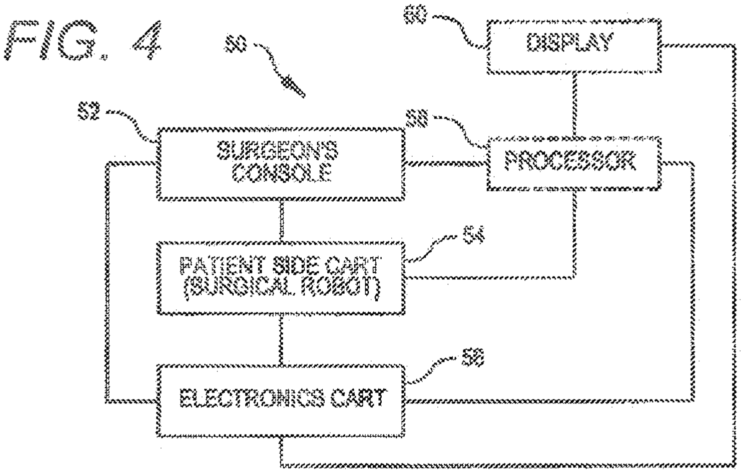
FIG. 4 diagrammatically illustrates a tele-surgical system, in accordance with many embodiments.

FIG. 4 diagrammatically illustrates a tele-surgical system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patient Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the manipulator structures described herein. The software will often comprise a non-volatile media, and could also comprise a monolithic code but will more typically comprise a number of subroutines, optionally running in any of a wide variety of distributed data processing architectures.

Figure 5A:
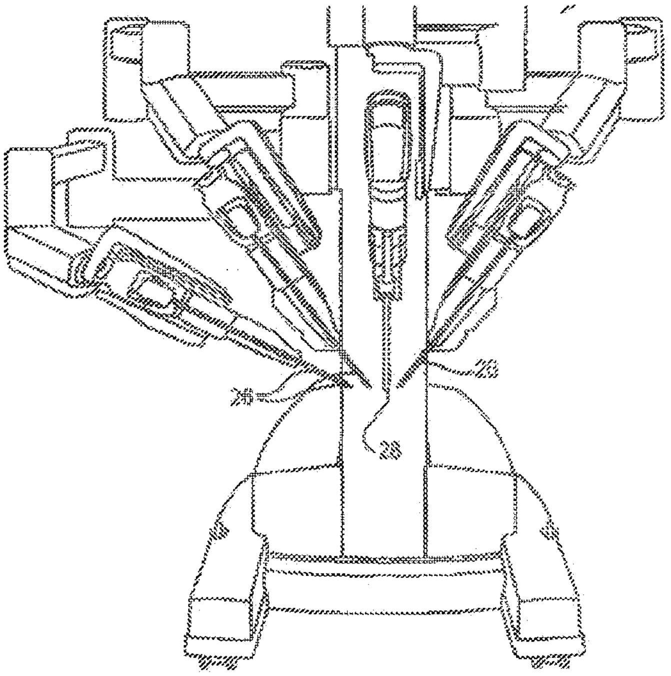
FIG. 5A is a partial view of a patient side cart (surgical robot) of a tele-surgical system, in accordance with many embodiments.
Figure 5B:
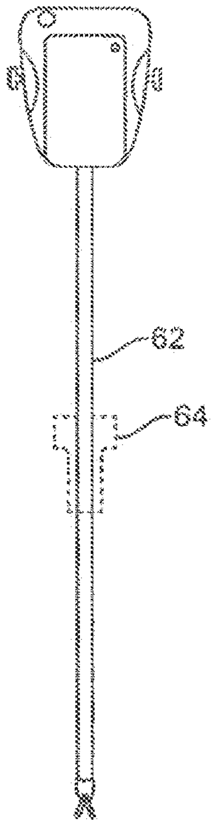
FIG. 5B is a front view of a tele-surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by manipulator mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the manipulator arm and the shaft of surgical tool 26 passes through the lumen of the cannula. The manipulator arm may transmit signals indicating that the cannula has been mounted thereon.

Tele-Surgical Systems and Modular Manipulator Supports

Figure 6:
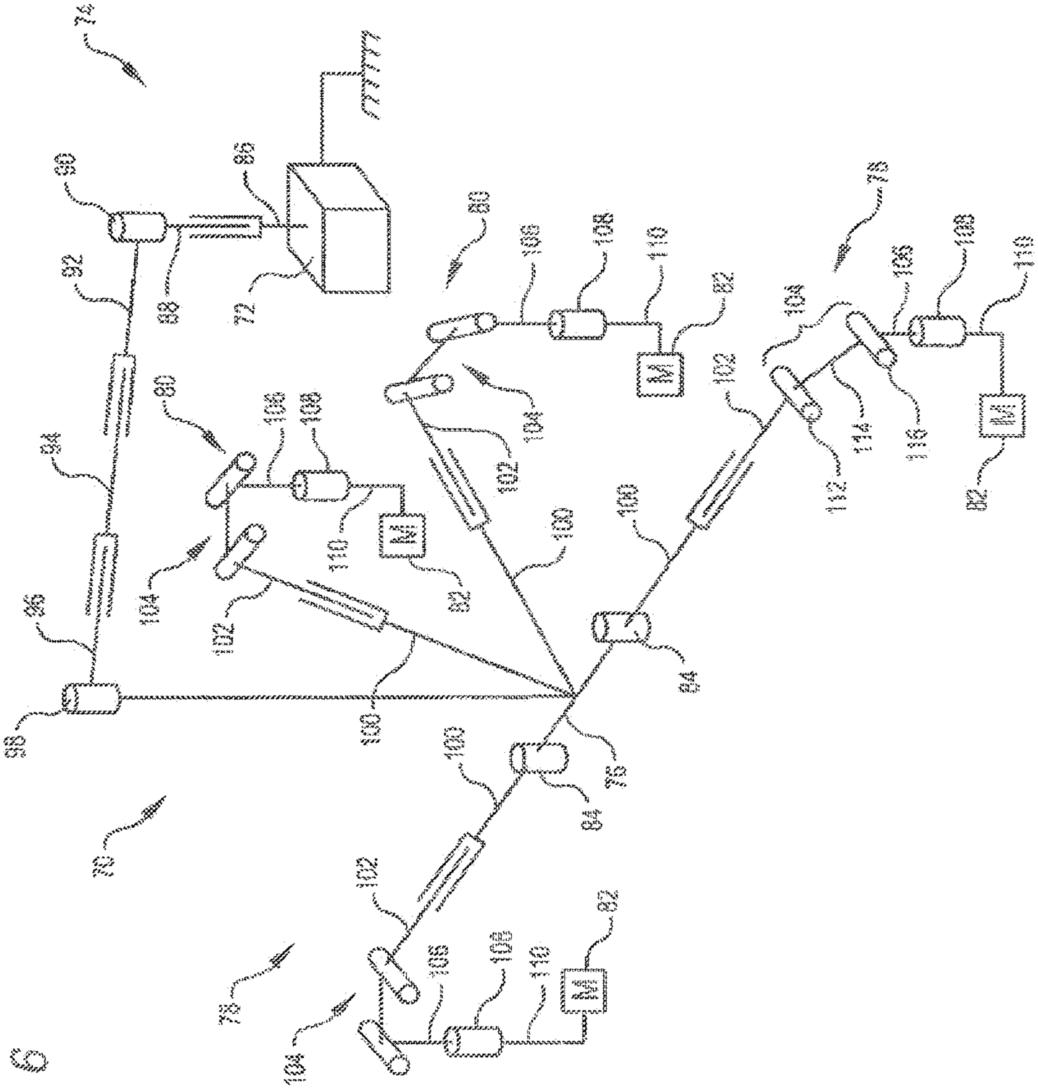
FIG. 6 is a perspective schematic representation of a tele-surgical system, in accordance with many embodiments.

FIG. 6 is a perspective schematic representation of a tele-surgical system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76.

Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
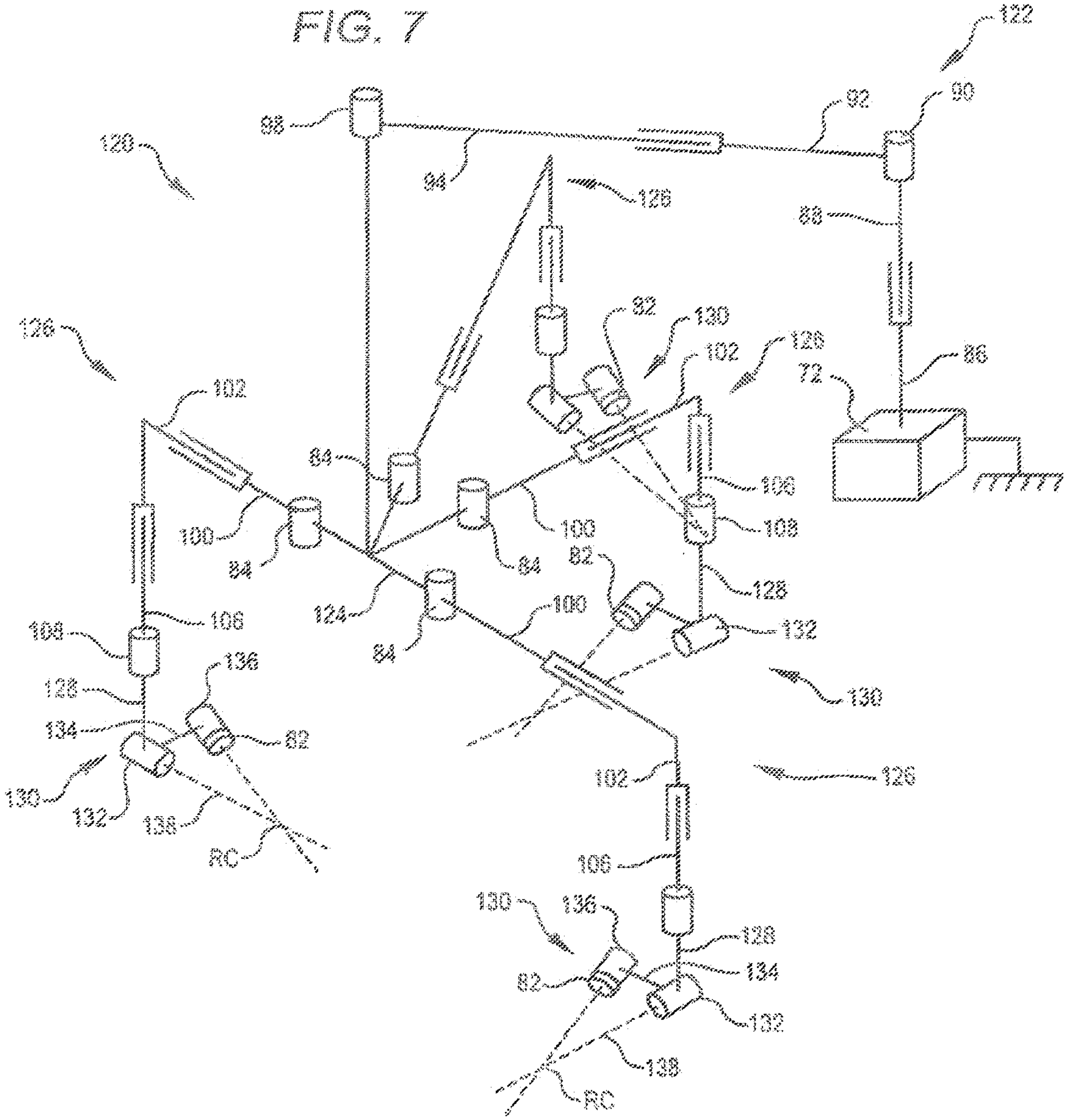
FIG. 7 is a perspective schematic representation of another tele-surgical system, in accordance with many embodiments.

FIG. 7 is a perspective schematic representation of a tele-surgical system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
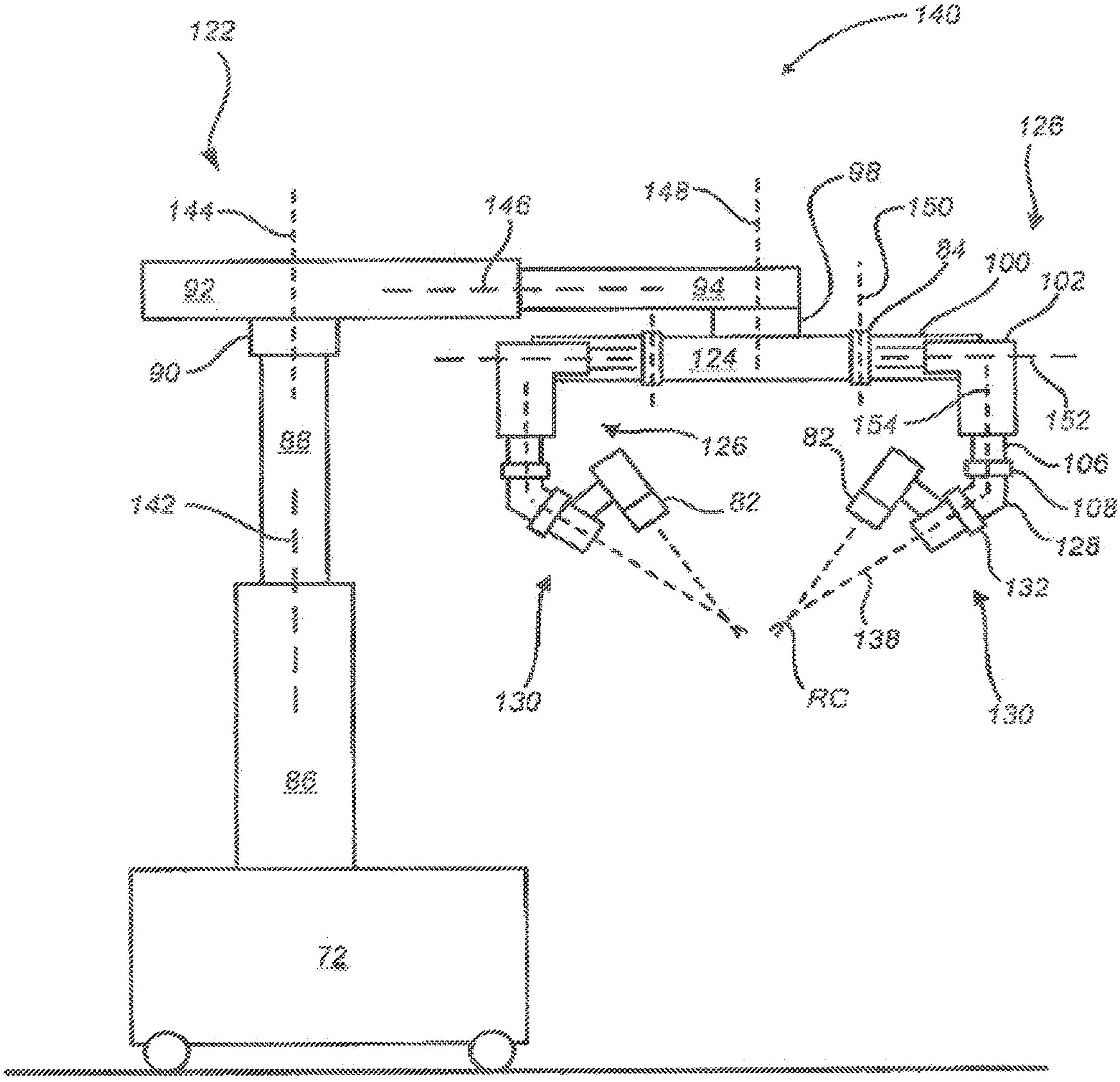
FIG. 8 shows a tele-surgical system, in accordance with many embodiments, in conformance with the schematic representation of FIG. 7.

FIG. 8 is a simplified representation of a tele-surgical system 140, in accordance with many embodiments, in conformance with the schematic representation of the tele-surgical system 120 of FIG. 7. Because the surgery system 140 conforms to the tele-surgical system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. The wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
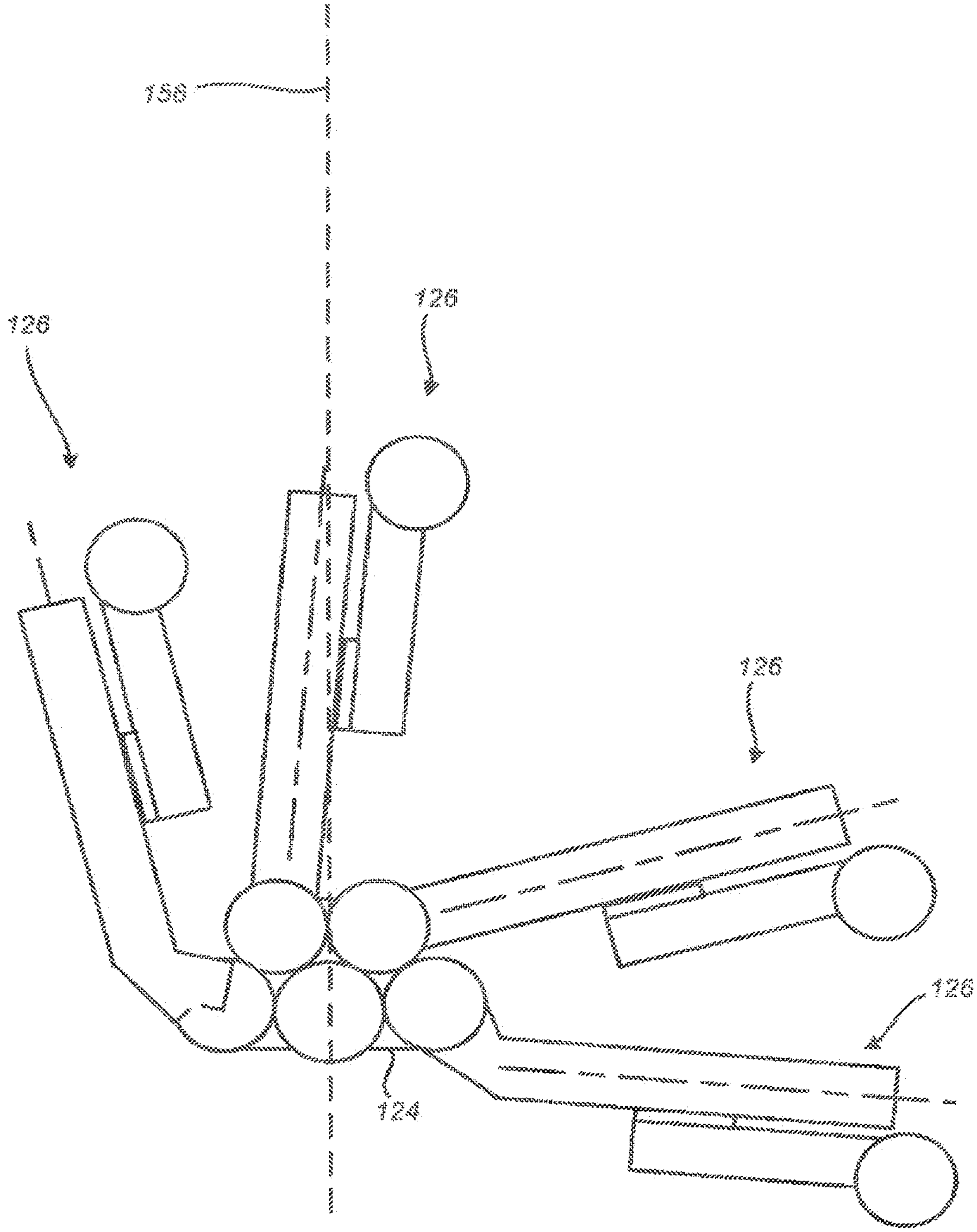
FIG. 9 illustrates rotational orientation limits of set-up linkages relative to an orienting platform of the tele-surgical system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

In use, it will often be desirable for a surgical assistant, surgeon, technical support, or other user to configure some or all of the linkages of tele-surgical system 140 for surgery, including the set-up structure linkage, the set-up joints, and/or each of the manipulators. Included among the task in configuring these linkages will be positioning the orienting platform 124 relative to first stage member 94 about vertical fourth SUS axis 148 of wrist joint 98. A joint drive motor 121 and/or brake system 123 is coupled to wrist joint 98, with one exemplary embodiment including both a drive 121 and brake 123. Additionally, a joint sensor system will typically sense an angular configuration or position of wrist joint 98.

An exemplary user interface, system, and method for manually configuring the system for use will be described herein with reference to manual articulation of orienting platform 124 by articulation of wrist joint 98 about fourth SUS axis 148, as schematically illustrated by arrow 127. It should be understood that alternative embodiments may be employed to articulate one or more alternative joints of the overall kinematic system, including one or more alternative joints of the set-up structure, one or more of the set-up joints, or one or more of the joints of the manipulators linkages. Use of the exemplary embodiment for articulating the motorized wrist joint embodiments may allow a user to efficiently position manipulators 82. The manual articulation of wrist joint 98 as described herein can improve speed and ease of use while manually docking manipulators 82 to their associated cannulas 64, as shown in FIG. 5B.

Figure 10:
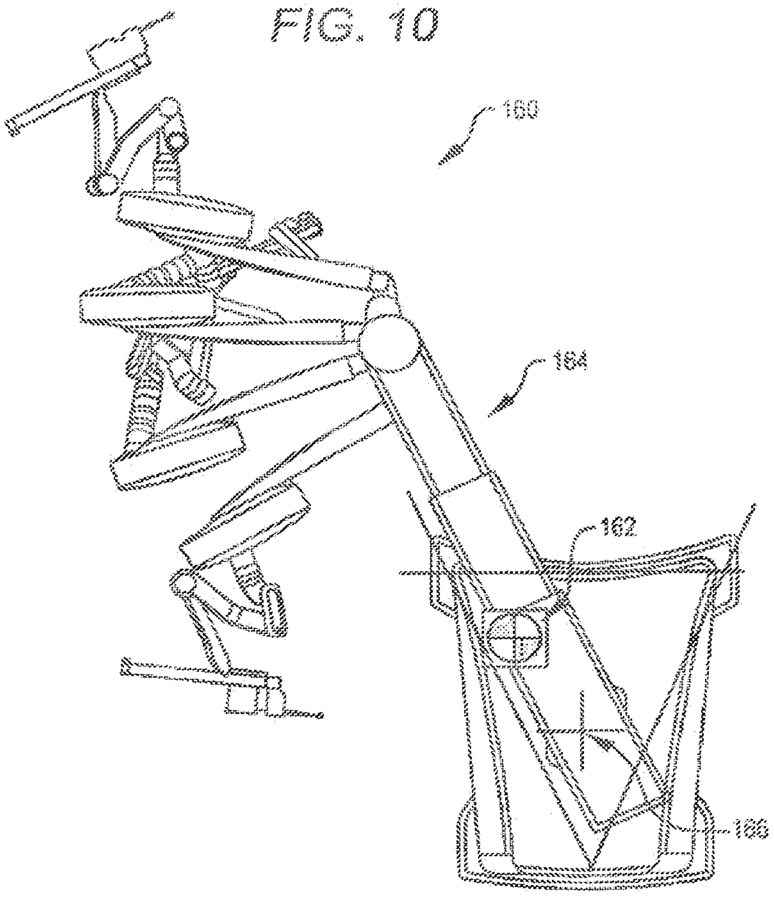
FIG. 10 shows a center of gravity diagram associated with a rotational limit of the boom assembly for a tele-surgical system, in accordance with many embodiments.

FIG. 10 shows a center of gravity diagram associated with a rotational limit of a support linkage for a tele-surgical system 160, in accordance with many embodiments. With components of the tele-surgical system 160 positioned and oriented to shift the center-of-gravity 162 of the tele-surgical system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 11:
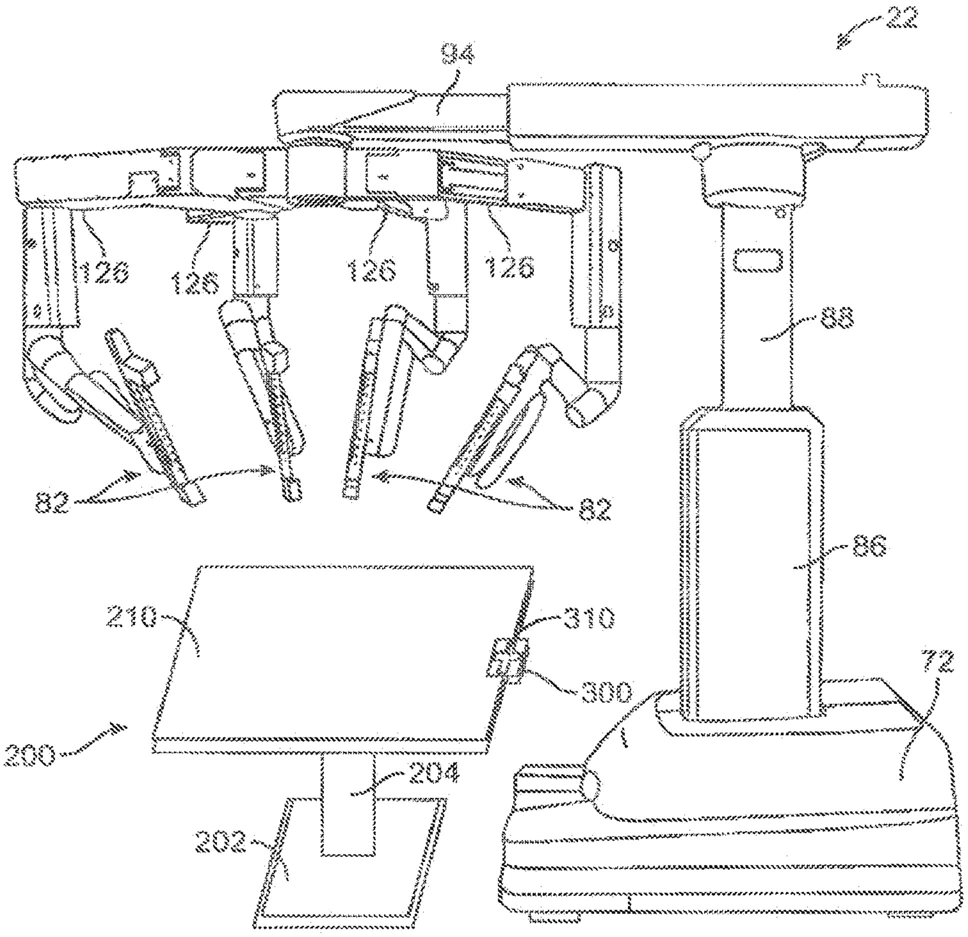
FIG. 11 shows an example manipulator assembly and positionable surgical table having a registration feature, in accordance with aspects of the invention.

FIG. 11 illustrates an overview of an example system including the Patient Side Cart 22 having multiple manipulator arms 82 supported by associated set-up structure linkages 126 under which a surgical table 200 is disposed. In certain aspects, the surgical table 200 is a separate structure from the Patient Side Cart such that the surgical table is separately positionable, and often independently positionable, from the Patient Side Cart. It is understood however, that in certain other aspects, the registration methods described herein allow for a separately positionable surgical table to be controlled in coordination with calculated movements of the manipulator such that the surgical table remains separately positionable but may no longer be considered independently positionable since such movements would be coordinated by the system. In many embodiments, surgical table 200 includes a surgical table patient support surface 210, supported by a support column 204 attached to a support base 202. The system further includes a registration feature 300 that allows the system to register the surgical table relative the Patient Side Cart such that a spatial relationship between the manipulators of the Patient Side Cart and the surgical table patient surface 210 can be determined and may be utilized in calculated manipulator movements or commanded surgical table movements. While the registration feature 300 may encompass various different structures, described and shown in subsequent figures, FIG. 11 illustrates a registration feature that includes a table-mounted registration device 310, described in further detail below.

Figure 12:
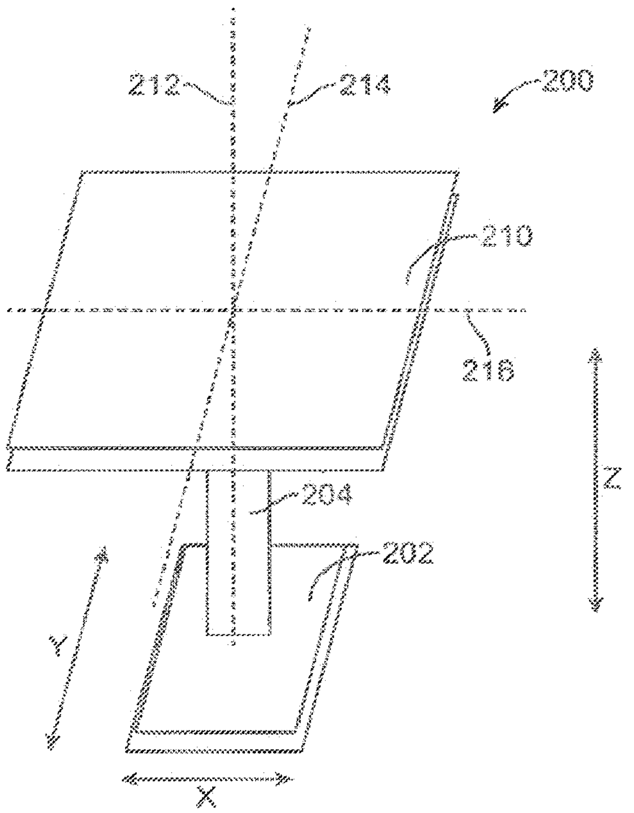
FIG. 12-13C show an example surgical table positionable along six degrees of freedom.

FIG. 12 illustrates an example surgical table 200 for use with a surgical manipulator system. The surgical table 200 may include one or more joints (not shown) that when actuated move the surgical table top to a desired position and/or orientation. The one or more joints may include driven joints, manually articulated joints, or a combination thereof. Such joints may include translatable joints, such as hydraulics, as well as rotatable and pivotal joints, such as any of those described herein. The one or more joints may be adjusted by a patient side-assistant or anesthesiologist, as needed, or may be configured to be adjusted by a more remote user, such as a physician from the Surgeon Console, or by the system according to an autonomous algorithm or according to one or more calculated movements, such as a compensating movement for physiological movements, such as patient breathing and the like.

Figure 13A:
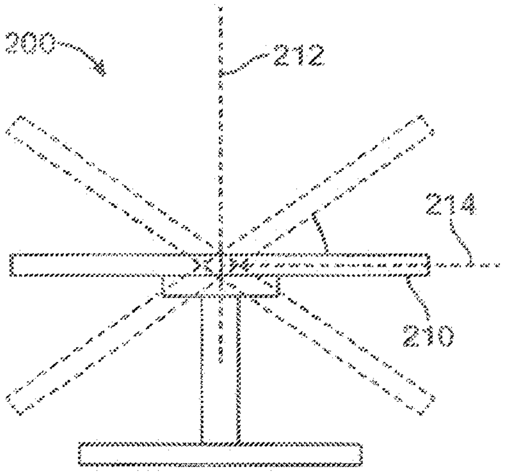
Figure 13B:
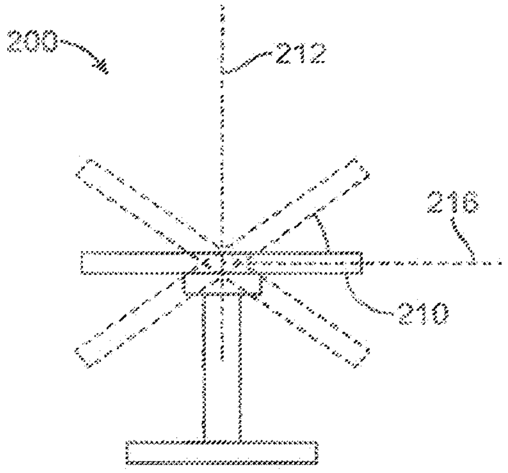
Figure 13C:
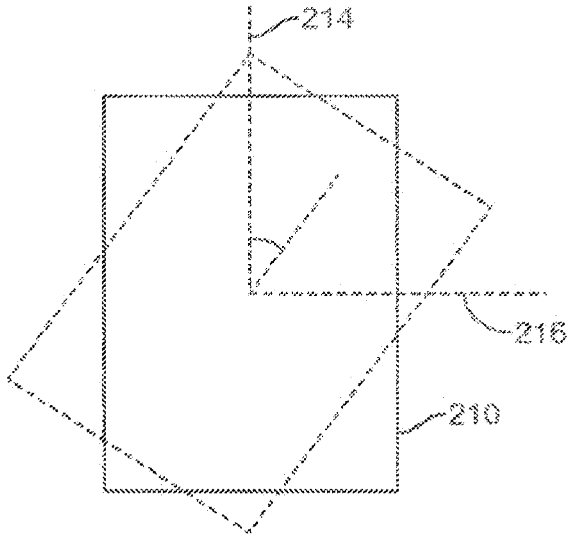

The surgical table 200 includes the surgical table patient support surface 210 supported by a support column 204 extending vertically from a support base 202. Typically, the surgical table 200 is positionable along at least one degree of freedom, preferably along multiple degrees of freedom, and even more preferably along six degrees of freedom. As shown in FIG. 12, the example surgical table 200 can be translated in three different directions orthogonal to one another, along the x-axis, the y-axis and vertically along the z-axis, and can be pivoted about axis 214 extending along the length of the patient support surface 210, pivoted about axis 216 extending along the width of the patient support surface 210 and pivoted about axis 212 extending vertically. Although the pivotal axes 212, 214 and 216 are shown intersecting at one point, these axes may not necessarily intersect. These pivotal movements are illustrated in FIGS. 13A-13C. Thus, the example surgical table 200 is positionable along six degrees of freedom. These various positions and/or orientations of the patient support surface 210 allowed by these six degrees of freedom may be utilized during initial set-up to achieve a desired position, orientation or inclination of the patent or may be utilized during a procedure as needed to reposition the patient for any reason. It is appreciated that the pivotal movements need not be centered along those particular axes shown, such that a table may provide such pivotal movements along various other axes in the same directions, thereby allowing the surgical table top to provide pivotal movements about various locations on or off the table top. In some embodiments, the surgical table is configured to provide such movements about an isocenter at or near a cannula through which an instrument is inserted within a minimally invasive aperture.

While the high degree of configurability of such a surgical table provides many advantages and versatility in positioning the patient, this configurability can further pose additional challenges in calculating movements of the manipulator arms and associated tools. For example, when the surgical table is positioned at an incline, certain movements of the tool or an associated manipulator supporting the tool may cause collisions with the patient or the patient support surface. While various methods may be used to avoid such collisions, it is particularly useful if the position of the surgical table relative to the manipulators of the Patient Side Cart is determined so that movements of the manipulators can be calculated to account for the position of the surgical table and/or to compensate for movement and/or repositioning of the surgical table during a procedure. To allow such a determination, methods and systems in accordance with aspects of the present invention provide registration between the surgical table and the Patient Side Cart so that a spatial relationship between the surgical table and Patient Side Cart can be determined and utilized in various calculated movements as needed.

Registration may be performed using various different approaches, for example approaches that include contact with the surgical table and approaches that do not require direct physical contact with the surgical table. While each of these approaches may offer certain advantages for particular systems or applications, it is appreciated that any aspect of these approaches may be modified and/or combined such that a method may include aspects of contact-based approaches in addition to non-contact based approaches. Examples of these approaches are described in further detail below.

Contact Based Registration

Manipulator Contact

In one approach, registration is performed by facilitated contact between the Patient Side Cart and the surgical table. Methods of registration may include contacting the surgical table at one or more locations with a component of the Patient Side Cart and determining a position and/or orientation of the surgical table relative the Patient Side Cart. This may be accomplished by determining the position and/or orientation of the surgical table relative to a frame of reference of the Patient Side Cart or a common frame of reference having a known or determinable relationship to both the Patient Side Cart and the surgical table.

In one aspect, contact with the surgical table may include contacting multiple locations with one or more location components associated with the Patient Side Cart so that the position and/or orientation of the surgical table can be determined by a determined state of the location component. A manipulator arm may function as the location component for registration purposes by using one or more joint sensors of the manipulator to determine a location of the contact point of the surgical table relative to the Patient Side Cart or corresponding frame of reference. If a geometry of the surgical table is known, the position and/or orientation of the surgical table can be determined with fewer points of contact, for example three points of contact. However, if a geometry of the surgical table is unknown, additional points of contact may be used to determine the bounds of the table, for example at least four contact locations (e.g. one contact location on each side or one contact location at each corner of a rectangular surgical table patient support surface). It is appreciated that the contact locations utilized may differ according to the table geometry. For example, certain surgical tables may include multiple planes that are movable relative each other (e.g. a dentist's chair) such that additional contact locations may be utilized to determine a position or orientation of the chair. Alternatively, sensed joint states of a chair having multiple planes may be used in conjunction with any of the registration features described herein to determine a position and/or orientation of the chair relative to the manipulator assembly.

Figure 14:
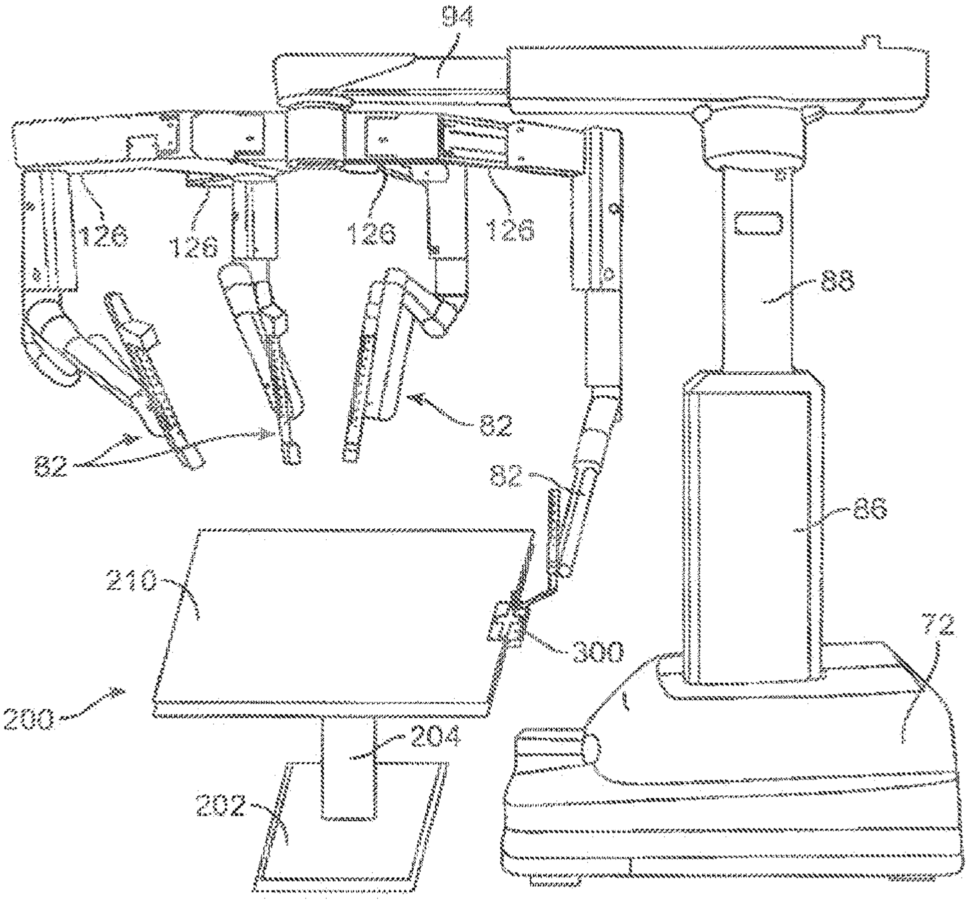
FIG. 14 shows an example manipulator assembly in FIG. 11 in which a manipulator arm is attached to the surgical table through the registration feature during registration.

In another aspect, contact with the surgical table may include contacting a single location with a location component and determining a position and/or orientation along one or more degrees of freedom of the surgical table by constraining movement of the location component along corresponding degrees of freedom. For example, as shown in FIG. 14, the registration feature 300 is a table-mounted registration device 310 to which a distal portion of a manipulator 82 can be releasably coupled. When coupled with the registration device 310, movement of the manipulator 82 is constrained along multiple degrees of freedom such that the position and/or orientation of the surgical table in corresponding degrees of freedom of the surgical table can be determined from joint sensors of the manipulator.

Figure 15A:
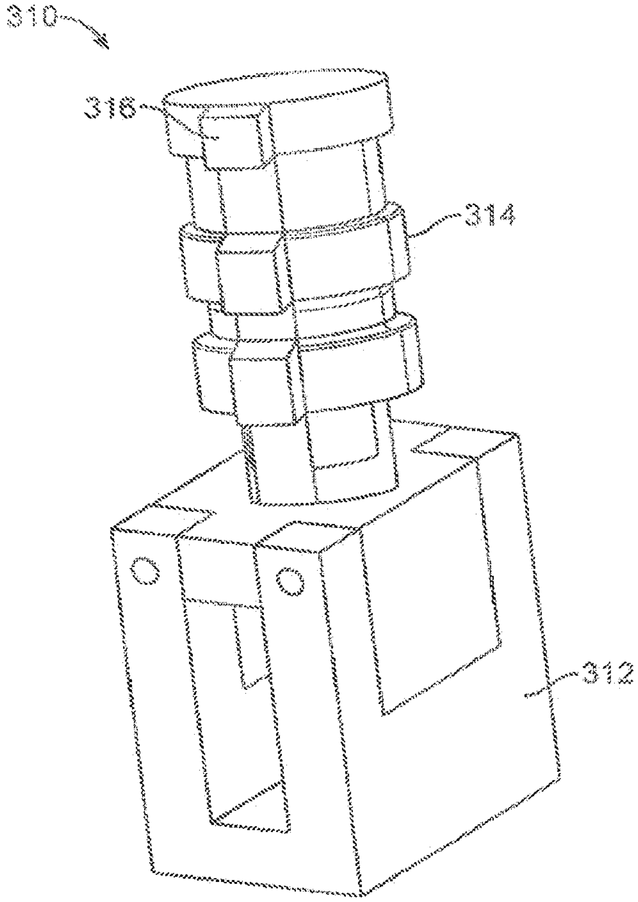
FIG. 15A-15B show an example registration device and a corresponding cannula, respectively, in accordance with aspects of the invention.
Figure 15B:
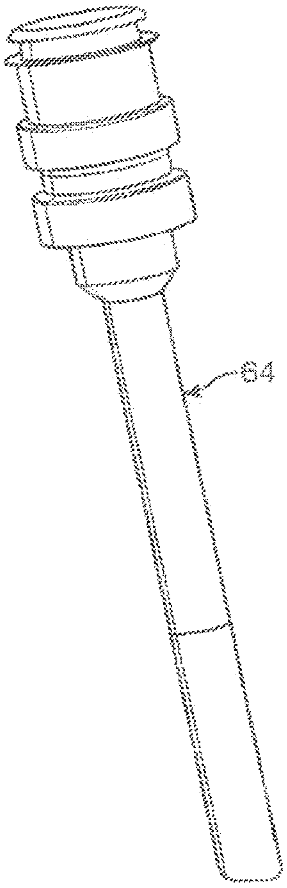

FIG. 15A illustrates an example table-mounted registration device 310 having a table-mount portion 312 and a cannula mount knob 314 configured for releasably coupling with a cannula mount of a distal portion of the manipulator 82. The cannula mount knob 314 may be a solid element cylindrical element shaped according to the dimensions of a cannula 64 (shown in FIG. 15B), for which the cannula mount of the manipulator 82 is designed to be attached. In one aspect, the knob is configured to be received within the cannula mount clamp described in U.S. Pat. No. 8,182,469, the entire contents of which are incorporated herein for all purposes. This allows the existing cannula mount of the manipulator 82 to couple to the registration device 310 so that the manipulator can function as a location component, the joint state sensors being used to determine the location and orientation of the table by the directions in which movement of the manipulator is constrained. As can be appreciated by referring to FIG. 15B, movement of the cannula mount portion of the manipulator is constrained in each of the translational directions, as well as in each of the pivotal directions (i.e. yaw, roll and pitch). The cannula mount knob 314 includes a table-mount portion 312 that mounts to a side-bar of the surgical table and an orientation key 316 that protrudes radially outward from the knob 314 so as to constrain rotational movement of the cannula mount so that each of the six degrees of freedom of the surgical table can be determined from the joint state sensors of the manipulator when attached to the table through the registration device. While this feature is described within the context of the cannula mount of the manipulator, it is appreciated that the registration device 310 may be configured to attach to any portion of any manipulator, of the Patient Side Cart or a component (even a temporarily attached component) extending therebetween so as to allow determination of a spatial relationship between the surgical table and the Patient Side Cart and associated manipulators.

Figure 16A:
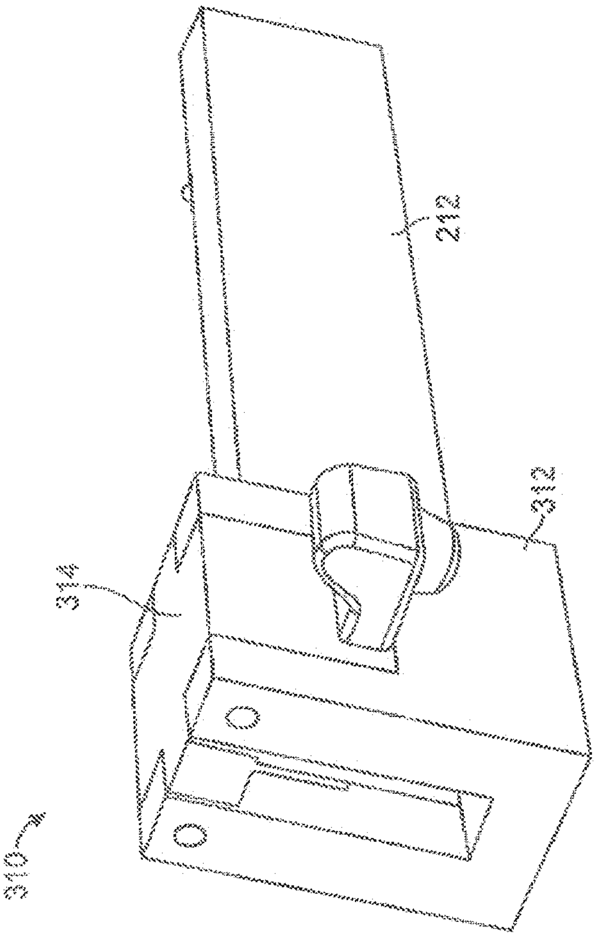
FIG. 16A-16B show an example registration device and a corresponding cannula, respectively, in accordance with aspects of the invention.
Figure 16B:
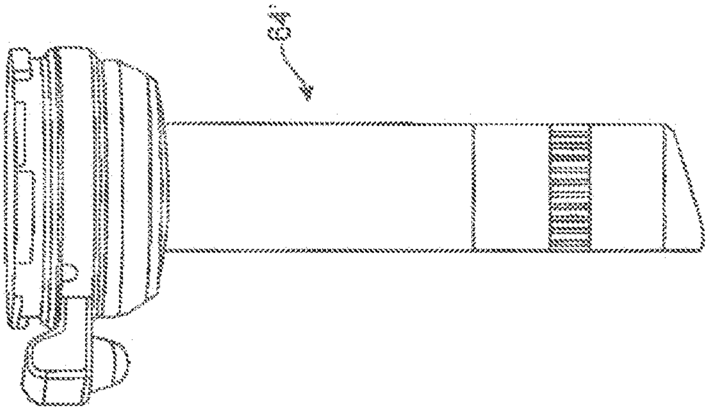
Figure 17A:
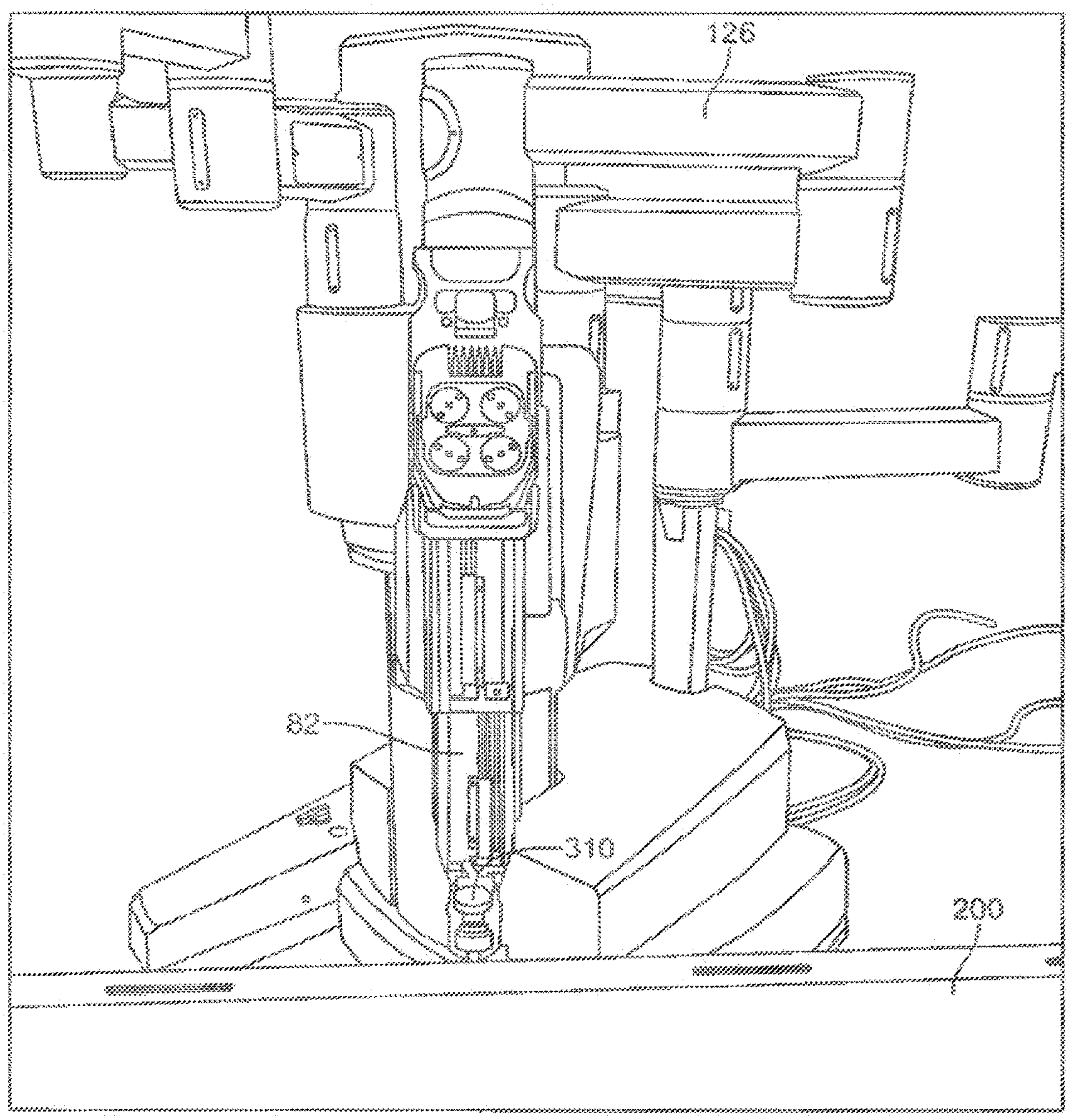
FIG. 17A-17D show a manipulator of a manipulator assembly attached to the surgical table through an example registration device, in accordance with aspects of the invention.
Figure 17B:
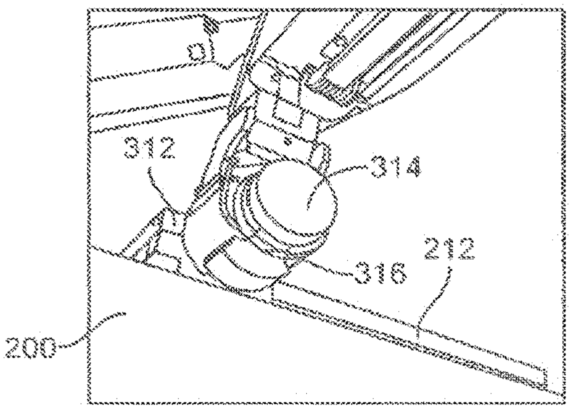
Figure 17C:
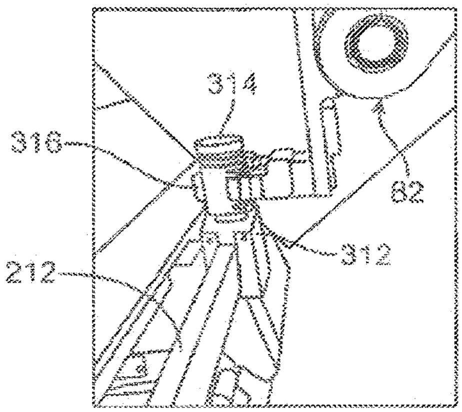
Figure 17D:
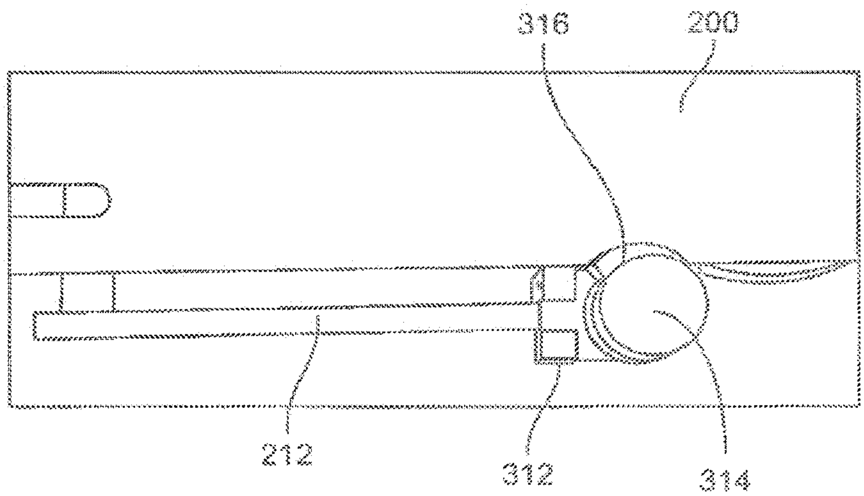

FIG. 16A illustrates another example table-mounted registration device 310 having a table-mount portion 312 and a cannula mount element 314' corresponding to another type of cannula 64.' Thus, the approach described in FIG. 15A can be used in various types of manipulator systems by fabricating a table-mounted registration device to resemble a cannula used in a particular manipulator system to allow registration using existing features of the system. FIG. 16A also further details the means by which the table-mounted device 310 attached to the table. While the table-mounted registration device can be attached to the surgical table by various means, it is particularly useful if such a device can be attached without requiring modification of or installation of additional structures to the table. For example, in surgical tables having a side bar 212 mounted on one or both sides of the surgical table patient support surface 210, the registration device 310 may include a side-bar mount 312 that mounts to the side-bar by engaging the side-bar as well as the support by which the side-bar mounts to the table. Such a side-bar 212 typically mounts to the surgical table by two such lateral supports near opposite ends of the side bar such that in a surgical table having side-bars 212 on both sides, there would be four such locations at which such a registration device 310 could be mounted (see for example FIG. 18).

Figure 18:
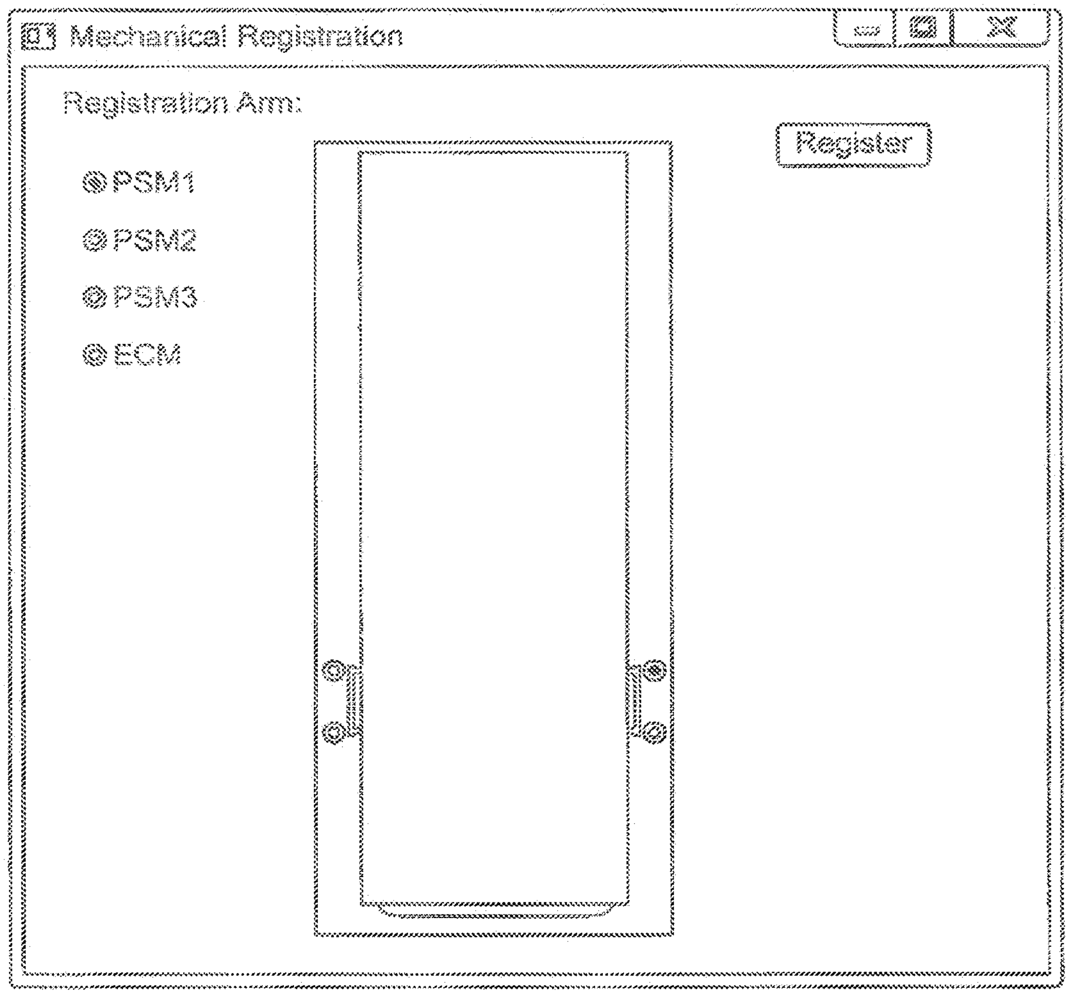
FIG. 18 shows an example dialog box in a user interface for inputting a location of the table to which the registration device is attached and to identify which manipulator is attached to the table through the device, in accordance with aspects of the invention.

In certain aspects, by attaching the table-mounted device 310 to the table at a known location, the position and/or orientation of the table can be more accurately determined using a known or estimated geometry of the table. For example, as shown in FIG. 18, if there are four possible locations on the table at which the registration device 310 can be attached, then the position and/or orientation of the table can be accurately determined, typically within less than one centimeter or less, using a known geometry of the surgical table and the joint state sensor data from the manipulator attached to the registration device 310 mounted to the table at known location. In one aspect, the system may be configured such that a user inputs the location of the table to which the registration device is attached as well as which manipulator is coupled with the registration device (for example, by use of a dialog box prompt shown in FIG. 18). In another aspect, the system may automatically detect, such as by use of a mechanical means, RFID, sonar or optical sensing means, at which location of the table the registration device 310 is attached as well as which manipulator is coupled with the registration device 310.

FIGS. 17A-17D illustrate additional views of the table-mounted registration device 310 similar to that in FIG. 15A, which is mounted to a side-bar 212 of the surgical table and to which the cannula mount of a manipulator is mounted to facilitate registration between the surgical table and the Patient Side Cart.

Linear Encoders

Figure 20:
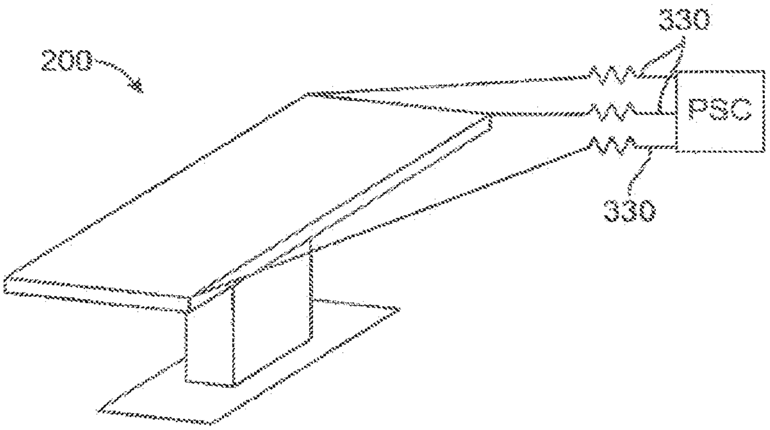
FIG. 20 shows a surgical table having a registration feature that includes three linear spring-encoders attached to the table.

In an alternative contact based approach, spring-loaded linear encoders can be mounted on the Patient Side Cart. As illustrated in FIG. 20, each of the spring-loaded linear encoders 330 can be stretched and attached to hooks on the side of the table so as to extend between the surgical table and the Patient Side Cart, or an associated component. In one aspect, at least three linear encoders are used so that readings from the linear encoders can be triangulated to determine the position and pose of the surgical table relative Patient Side Cart and surgical table. It is further appreciated that such encoders can also be used extending between the surgical table and an external frame of reference, such as the floor of the surgical room, to allow registration through a common external frame of reference. This approach can be used initially within a pre-docking registration or such encoders can remain attached so as to allow determination of the position and/or orientation of the surgical table during the procedure and maintain registration throughout the procedure without otherwise requiring use of one of the manipulators.

Non-Contact Based Registration

Shape Sensors

Figure 19:
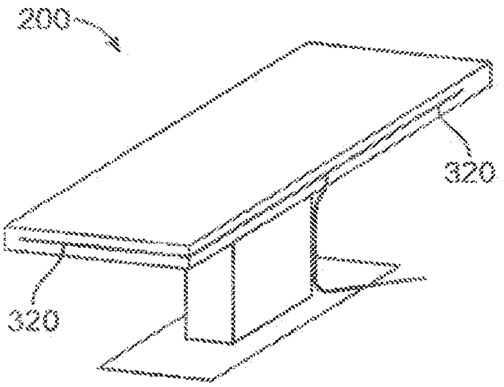
FIG. 19 shows a surgical table having a registration feature that includes a cable shape sensor attached to the table.

In one approach, the system may utilize a flexible arm equipped with shape sensors. In certain aspects, the shape sensor is a hose-like object hanging on the side of the Patient Side Cart which has a tip that can be locked to the side of the table. The locking mechanism has sensors which detect connection/disconnection. Shape sensors (e.g., optical shape sensing fibers) are used in the flexible arm to measure its shape when it is connected to the table. Shape information can be used to calculate the relative pose of the Patient Side Cart with respect to the table. In another aspect, the shape sensor, such as a cable shape sensor, optical fiber, flex or position orientation sensing member, can be attached or locked to a side of the table, such that the position and/or orientation can readily be determined by the system based on input from the shape sensor. An example embodying this approach is illustrated in FIG. 19, which shows a shape cable sensor 320 extending attached to two sides of the surgical table so as to allow for determination of a position and pose of the surgical table from a sensed output from the shape cable. This is advantageous as the shape sensor allows the position and/or orientation to be dynamically sensed during a procedure such that registration between the manipulators and surgical table is substantially continuous during a procedure.

It is appreciated that, in regard to the use of shape sensors, the methods of registration described herein may further include any of the aspects described in U.S. Application No. 7,930,065 filed Jul. 20, 2006, entitled "Robotic Surgery System Including Position Sensors Using Fiber Bragg Gratings," the entire contents of which are incorporated herein for all purposes.

In certain aspects, one or more shape sensor cords can be attached to one or more particular locations of the surgical table to allow the system to determine a position and/or orientation of the table. In another aspect, shape sensor cables may be incorporated into the cables by which the Patient Side Cart and the surgical table are powered such that the Patient Side Cart can be registered to one another through an external frame of reference, such as the surgical operating room to which the cords are attached. In another aspect, the system may utilize such a shape sensor cord extending directly between the Patient Side Cart and the surgical table, which can be used for registration purposes, in addition to various other purposes.

Optical/Radiation Sensing

Figure 21:
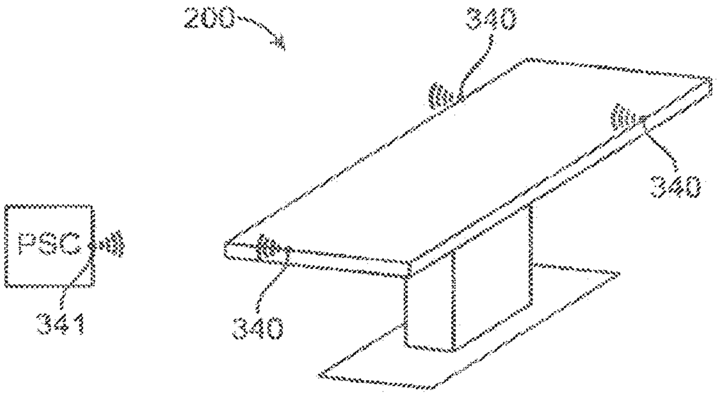
FIG. 21 shows a surgical table having a registration feature that includes three markers for sensing with an external sensor associated with the manipulator assembly or a common frame of reference.

In another approach, various other non-contact means may be used by which to determine a position and/or orientation of the surgical table relative the Patient Side Cart. Such means may include any of optical or radiation sensing means, sonar, laser range sensors, or any other suitable means. In one aspect, such sensing means can be attached to the Patient Side Cart and configured to sense one or more points on the surgical table (e.g. RFID tags, identifiable optical or laser markers) such that the position and/or orientation of the table relative the Patient Side Cart can be determined before and/or during the procedure. This approach, particularly when using RFID tags, may be on one or both of the surgical table and the Patient Side Cart to determine absolute locations or relative locations between the surgical table and the Patient Side Cart so as to allow for registration therebetween. An example of this approach is illustrated in FIG. 21, which show an RFID sensor 341 attached to the Patient Side Cart (not shown) that can sense a position of each of three RFID tags 340 attached to the table at various locations. By triangulating the signals from each of the RFID tags, the position and pose of the surgical table can be determined.

It is further appreciated that this approach can also be used to allow registration through a common external frame of reference, such as by sensing the RFID location from an external reference frame, such as a known location in the surgical room. For example, the methods described herein may perform registration using absolute location or relative location for real-time location using point-to-point distance determination between multiple RFID tags or various other real-time location approaches.

Registration Work Flow

Pre-Docking Registration

In one aspect, methods of registration include a pre-docking registration. Prior to docking the surgical manipulators to a patient on the patient support surface of the surgical table, a manipulator arm is docked to a table-side mounted registration device 310 (such as in FIG. 15A or FIG. 16A). By reading encoder values of the Patient Side Manipulator (PSM) and Set-up Joints (SUJs) ($q_{robot}$) and solving and a rigid body kinematic problem, the position and orientation of the surgical robot (i.e., Patient Side Cart) can be resolved with respect to the registration device 310. As detailed above, the registration device 310 is configured such that it can only be attached to the table in a unique way, that is at one or more particular locations of the table at a particular alignment/orientation relative to the table (e.g. such as at one of four locations where the side rails connect to the table top). Therefore the pose of the gadget with respect to the table can readily be determined, such as from CAD models of the table geometry or from a calibration of the table top using one or more sensors or an external tracker. In another aspect, the surgical operating table can be motorized and encoders can be used with the actuation joints of the table ($q_{table}$) to provide its position and orientation.

In one aspect, the position and orientation of the manipulator assembly can be resolved with respect to the surgical operating table, often the base of the surgical operating table assumed as the world coordinate system, using the following equation:

$$T_{World}^{PSC} = T_{World}^{Table}(q_{table}) \cdot T_{Table}^{Gadget} \cdot T_{Gadget}^{PSC}(q_{robot})$$

Typically, pre-docking registration between the Patient Side Cart and the surgical operating table would be performed once before a procedure, after which generally the Patient Side Cart (PCS) would not be moved since this may necessitate another registration during the procedure in which the manipulators would be undocked, another registration performed and then re-docking the manipulators with the patient.

Continuous Monitoring of Patient Side Cart Motions

In another aspect, the manipulator used for registration may remain docked during the entire procedure such that registration would be substantially continuous allowing movement of the surgical table during a procedure without requiring performing of additional registration steps during the procedure. One drawback with this approach is that the use of one manipulator may be lost such that this approach may not be suitable for a procedure utilizing each of the manipulators. In such procedure, any of the alternative technologies or approaches described herein may be utilized to perform registration in accordance with aspects of the invention.

In manipulator systems having a plurality of manipulator arms, one possible scenario is to leave one of the manipulator arms connected to the registration gadget during the operation. In such cases, it is possible to detect any motion of the Patient Side Cart and generate alarms if the Patient Side Cart has moved during the operation. In one aspect, this can be done, by (a) releasing Setup Joint (SUJ) brakes and monitoring their encoder values or (b) monitoring the torque on Set-Up Joints and manipulator joints or a combination thereof.

Coordinated Motion of Surgical Table and Manipulators

In certain systems, when a mobile surgical manipulator is docked to the patient, generally, it is not feasible to move the table. If table motion is needed for any reason (including reorienting the patient), generally, a user must undock the manipulators from the patient, move the table and then re-dock the manipulators with the patient. By using a manipulator arm that remains attached to the table through a registration device mounted on the surgical table during the procedure, the system creates a closed kinematic chain between the robot and the table. This can be used to perform a real-time registration of the surgical table and the manipulator assembly. Therefore, if the surgical table is moving, any manipulator arms docked with the patient can be moved accordingly and there is no need for undocking the robot. Thus, by use of the registration approaches described herein, a separately positionable surgical table can be incorporated into a surgical system having a manipulator assembly such that movements between the surgical table and the manipulator assembly can be coordinated such that further advantageous features may be realized.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. A method comprising:

receiving at least one sensor reading that indicates a position or an orientation of a manipulator arm of a manipulator assembly when a keying feature of a distal portion of the manipulator arm is in contact with and received by a key receiving feature of a registration element of a table mounted registration device mounted to a side of a surgical table between a top surface and a bottom surface of the surgical table, wherein the distal portion of the manipulator arm is movable in a plurality of degrees of freedom;

determining, based on the received at least one sensor reading, a spatial relationship between the manipulator assembly and the table mounted registration device; and reducing, by the table mounted registration device, the plurality of degrees of freedom when the table mounted registration device is in contact with and receives the distal portion of the manipulator arm.

2. The method of claim 1, further comprising:

calculating, by a control system, a movement of the manipulator assembly based on the spatial relationship between the manipulator assembly and the table mounted registration device.

3. The method of claim 1, further comprising:

receiving a user input identifying the manipulator arm.

4. The method of claim 1, further comprising:

receiving a user input providing information about a location of the surgical table relative to the manipulator assembly.

5. The method of claim 1, wherein:

the manipulator assembly is associated with a manipulator assembly reference frame;

the table mounted registration device is associated with a surgical table reference frame; and the manipulator assembly reference frame is movable relative to the surgical table reference frame.

6. The method of claim 1, wherein reducing the plurality of degrees of freedom includes reducing the plurality of degrees of freedom by multiple degrees of freedom when the registration element is in contact with and receives the distal portion of the manipulator arm.

7. A method comprising:

receiving at least one sensor reading that indicates a position or an orientation of a manipulator arm of a manipulator assembly when a keying feature of a distal portion of the manipulator arm is in contact with and received by a key receiving feature of a registration element of a table mounted registration device mounted to a surgical table, wherein the key receiving feature of the registration element comprises a protrusion extending in a direction radially outward from a central axis of the registration element, and wherein the distal portion of the manipulator arm is movable in a plurality of degrees of freedom;

determining, based on the received at least one sensor reading, a spatial relationship between the manipulator assembly and the table mounted registration device; and reducing, by the table mounted registration device, the plurality of degrees of freedom when the table mounted registration device is in contact with and receives the distal portion of the manipulator arm.

8. The method of claim 7, wherein reducing the plurality of degrees of freedom comprises reducing the plurality of degrees of freedom when a curved surface of the registration element of the table mounted registration device is in contact with a curved surface of the distal portion of the manipulator arm.

9. The method of claim 7, wherein reducing the plurality of degrees of freedom comprises reducing the plurality of degrees of freedom when an at least partially cylindrical surface of the registration element of the table mounted registration device is in contact with an at least partially cylindrical surface of the distal portion of the manipulator arm.

10. The method of claim 7, further comprising:

calculating a movement of the manipulator assembly based on the spatial relationship between the manipulator assembly and the table mounted registration device.

11. The method of claim 7, further comprising:

immobilizing the manipulator arm when the spatial relationship between the manipulator assembly and the table mounted registration device is established.

12. The method of claim 7, further comprising:

receiving a user input identifying the manipulator arm.

13. The method of claim 7, further comprising:

determining the position or the orientation of the manipulator arm using the at least one sensor reading and rigid body kinematics.

14. A method comprising:

receiving at least one sensor reading that indicates a position or an orientation of a manipulator arm of a manipulator assembly when a distal portion of the manipulator arm is, via a keyed connection, in contact with and received by a registration element of a table mounted registration device mounted to a side of a surgical table between a top surface and a bottom surface of the surgical table, wherein the distal portion of the manipulator arm is movable in a plurality of degrees of freedom;

determining, based on the received at least one sensor reading, a spatial relationship between the manipulator assembly and the table mounted registration device; and reducing, by the table mounted registration device, the plurality of degrees of freedom when the table mounted registration device is in contact with and receives the distal portion of the manipulator arm.

15. The method of claim 14, wherein reducing the plurality of degrees of freedom comprises reducing the plurality of degrees of freedom when a curved surface of the registration element of the table mounted registration device is in contact with a curved surface of the distal portion of the manipulator arm.

16. The method of claim 14, wherein reducing the plurality of degrees of freedom comprises reducing the plurality of degrees of freedom when an at least partially cylindrical surface of the registration element of the table mounted registration device is in contact with an at least partially cylindrical surface of the distal portion of the manipulator arm.

17. The method of claim 14, further comprising:

calculating a movement of the manipulator assembly based on the spatial relationship between the manipulator assembly and the table mounted registration device.

18. The method of claim 14, further comprising:

immobilizing the manipulator arm when the spatial relationship between the manipulator assembly and the table mounted registration device is established.

19. The method of claim 14, further comprising:

determining the position or the orientation of the manipulator arm using the at least one sensor reading and rigid body kinematics.

* * * * *